(12) United States Patent
Yuen et al.

(10) Patent No.: US 11,236,128 B2
(45) Date of Patent: Feb. 1, 2022

(54) METHOD OF PREPARING STAPLED PEPTIDES

(71) Applicant: Agency for Science, Technology and Research, Singapore (SG)

(72) Inventors: Tsz Ying Yuen, Jurong Island (SG); Charles William Johannes, Jurong Island (SG); Gerard Hilinski, Somerville, MA (US)

(73) Assignee: Agency for Science, Technology and Research, Singapore (SG)

(*) Notice: Subject to any disclaimer, the term of this patent is extended or adjusted under 35 U.S.C. 154(b) by 42 days.

(21) Appl. No.: 16/635,472

(22) PCT Filed: Jul. 31, 2018

(86) PCT No.: PCT/SG2018/050388
§ 371 (c)(1),
(2) Date: Jan. 30, 2020

(87) PCT Pub. No.: WO2019/027368
PCT Pub. Date: Feb. 7, 2019

(65) Prior Publication Data
US 2021/0139538 A1    May 13, 2021

(30) Foreign Application Priority Data
Jul. 31, 2017 (SG) .......................... 10201706224X

(51) Int. Cl.
  *C07K 7/08* (2006.01)
  *C01G 55/00* (2006.01)
  *C07K 1/04* (2006.01)
  *C07K 1/12* (2006.01)

(52) U.S. Cl.
CPC ............. *C07K 7/08* (2013.01); *C01G 55/00* (2013.01); *C07K 1/045* (2013.01); *C07K 1/12* (2013.01)

(58) Field of Classification Search
CPC .... C07K 14/001; C07K 1/04; C07K 14/4746; C07K 1/113; C07K 1/047; A61K 38/02; A07K 1/10
See application file for complete search history.

(56) References Cited

U.S. PATENT DOCUMENTS

2006/0008848 A1* 1/2006 Verdine ................ C07K 14/001
                                                             435/7.1

FOREIGN PATENT DOCUMENTS

WO    WO-2005044839 A2    5/2005
WO    WO-2012051410 A2    4/2012

OTHER PUBLICATIONS

Aihara, K. et al. (2015). "Liquid-Phase Synthesis of Bridged Peptides Using Olefin Metathesis of a Protected Peptide with a Long Aliphatic Chain Anchor," Organic Letters, 17:696-699.
International Search Report and Written Opinion dated Oct. 30, 2018 for PCT Application No. PCT/SG2018/050388 filed on Jul. 31, 2018, 7 pages.
Lacombe, P. et al. (1998). "Reduction of Olefins on Solid Support Using Diimide," Tetrahedron Letters, 39:6785-6786.

* cited by examiner

*Primary Examiner* — Sudhakar Katakam
(74) *Attorney, Agent, or Firm* — Morrison & Foerster LLP

(57) ABSTRACT

Described herein is an operationally simple, one-pot solid-supported preparation of saturated stapled peptides. Following completion of ruthenium-catalysed metathesis, solid-phase transfer hydrogenation was achieved using triethylhydrosilane at elevated temperatures. The utility of the method has been demonstrated on 14- and 16-mer peptides to yield the corresponding cyclic a-helix stabilised stapled peptides.

23 Claims, 3 Drawing Sheets

METHOD OF PREPARING STAPLED PEPTIDES

CROSS REFERENCE TO RELATED APPLICATIONS

This application is a national stage application under 35 U.S.C. § 371 of International Application No. PCT/SG2018/050388, filed internationally on Jul. 31, 2018, which claims the benefit of priority to Singapore Application No. 10201706224X, filed Jul. 31, 2017.

FIELD

This invention relates to a method of preparing saturated stapled peptides.

BACKGROUND

The concept of helix stabilisation by cross metathesis of 2 amino acid sidechains was first introduced by Grubbs et al. (FIG. 1A) (H. E. Blackwell, R. H. Grubbs; *Agnew. Chem., Int. Ed.* 1998, 37, 3281). This technology, later termed "stapled peptides", was further refined with the introduction of an all-hydrocarbon bridge (FIG. 1B).

It is well known that i, i+4 stapling exclusively forms the cis isomer, whereas i, i+3 and i, i+7 stapling affords mixtures of cis/trans isomers. Stereoisomerism may be resolved by an additional hydrogenation step (Step-2, FIG. 1B). When stapled, the peptides are intramolecularly bound via an alkenyl linker to produce an unsaturated stapled peptide. However, saturated stapled peptides may, in some instances, be preferred.

Heterogeneous catalysts (Pd/C, $PtO_2$ and Ra—Ni) are routinely employed in the transformation of alkenes to alkanes. Unfortunately, due to poor kinetics in solid-solid interactions, these common catalysts have little use in solid-supported reactions. Instead, in-situ generation of diimine from sulfonyl hydrazides has previously been used to affect transfer hydrogenations of resin-bound unsaturated peptides.

More recently, tandem on-resin ruthenium-catalysed cross-metathesis/reduction sequences have been described. For instance, the reduction of α,β-unsaturated alkenes with Grubbs II catalyst and triethylhydrosilane under microwave irradiation has been reported (FIG. 2A), as has the successful synthesis of a library of alkylated tetrapeptides by a one-pot isomerisation-cross metathesis-reduction process (FIG. 2B). The utility of non-silane-type transfer hydrogenation reagents has also been demonstrated using sodium borohydride derivatives under solution phase conditions (FIG. 2C).

Whilst recent publications on the topic of tandem metathesis/transfer hydrogenation seemed promising, two more recent publications have described conditions for cross-metathesis/hydrogenations of relatively simple substrates that are unlikely to form aggregates on resin. As one of the biggest problems with on-resin peptide synthesis is potential aggregation of the growing peptide within the resin matrix, it remains to be seen whether the conditions will be well-suited for complex, hydrophobic macrocycles. Similarly, transfer hydrogenation using sodium borohydride has been demonstrated in solution phase only.

It has previously been found that the recommended in-situ diimine reductions known in the art to produce saturated stapled peptides are sluggish, impractical and costly. For instance, the attempted hydrogenation of stapled peptide PM2 after 4×2 h treatments with 2,4,6-triisopropylbenzenesulfonyl hydrazide only resulted in 50% product conversion (FIG. 3). Similar results were obtained for stapled peptides ATSP-7041 and VIP116, with respective yields of 39% and 45% after 3 treatments with the reagents.

Currently known stapled peptide reduction processes require repeated exposure of the resin-bound alkene to 2,4,6-triisopropylbenzenesulfonyl hydrazide/piperidine until the reaction has proceeded to an acceptable level. Generally, 5 treatments are recommended at a minimum with this scheme. In order to determine the rate of reaction, the reaction mixture is filtered and a small sample of resin beads is treated with TFA to cleave the peptide from the solid support, which is then analysed by HPLC-LCMS. Not only is the entire process cumbersome and impractical, the high cost of reagents such as 2,4,6-triisopropylbenezenesulfonyl hydrazide becomes a major influence in determining how far a reaction should be taken. Taking into account the severe limitations of current technologies, alternative hydrogen transfer strategies to access saturated stapled peptides on resin are needed.

SUMMARY OF INVENTION

In a first aspect of the present invention there is provided a process for producing a compound of general Formula I:

$$P^1\text{—}B^1\text{—}A_m\text{—}B^2\text{—}P^2\text{—}H \quad \text{I}$$

wherein:

m is an integer between 1 and 8;

each A is independently an amino acid residue;

$B^1$ and $B^2$ are each substituted amino acid residues covalently coupled together by a saturated alkyl chain;

$P^1$ and $P^2$ are each independently one or more amino acid residues, wherein $P^1$ has a terminal amino group and $P^2$ has a terminal carboxylic acid group; and, H is hydrogen;

said process comprising the steps of:

a) performing a metathesis reaction on a compound of general Formula II so as to form an intramolecular alkenyl chain between the $B^{1a}$ and $B^{2a}$ groups $$P^1\text{—}B^{1a}\text{-}A_m\text{-}B^{2a}\text{—}P^2\text{—}S \quad \text{II}$$

wherein:

$B^{1a}$ is a group of Formula IIa wherein $R^1$ is alkyl;

$B^{2a}$ is a group of Formula IIb

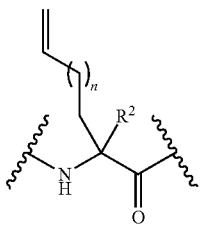

wherein $R^2$ is alkyl;
each n is independently an integer between 0 and 12; and
S is a solid state resin;
said reaction occurring between the alkenyl side chain of $B^{1a}$ and the alkenyl side chain of $B^{2a}$ so as to form an intramolecular alkenyl chain;

b) hydrogenating the carbon-carbon double bond formed in step a) so as to produce a saturated alkyl chain; and, c) cleaving the solid state resin material from $P^2$ so as to produce a compound of Formula I.

The following options may be used in conjunction with the first aspect, either individually or in any suitable combination.

The m variable may be an integer between 1 and 6. Each A may independently be a naturally occurring L-α-amino acid. At least one A may be an unnaturally occurring amino acid. $R^1$ and $R^2$ may each be ethyl. S may comprise a polymeric material.

Step a) of the process of the first aspect may be a metathesis reaction. It may be conducted in the presence of a catalyst. The catalyst may comprise ruthenium. The catalyst added to a suspension of a compound of Formula II may be fresh. The fresh catalyst may be added in separate aliquots, for example fresh catalyst may be added in 2, 3, 4 or 5 aliquots during the reaction of step b). Fresh catalyst may be added to a compound of Formula II twice before conducting step b). The temperature that the metathesis reaction of step a) is conducted at may be between 15° C. and 60° C.

Step b) of the process of the first aspect may be a hydrogenation reaction. The hydrogenation reaction of step b) may use a hydrosilane reagent of Formula $SiH_nR_{4-n}$, where n=1, 2, 3 or 4 and R is an organic group. The hydrosilane reagent may be a trialkylhydrosilane reagent of general Formula $[R_3SiH]$, wherein R is alkyl. Each R may be independently selected from the group consisting of methyl, ethyl, propyl, butyl and pentyl. Each R may be ethyl. When each R is ethyl, the trialkylhydrosilane reagent is triethylhydrosilane.

The hydrogenation reaction of step b) may occur after the completion of step a), or it may occur simultaneously. When the reactions of step a) and step b) are conducted at the same time, the hydrosilane reagent may be added to the reaction mixture concomitantly with the catalyst. The hydrosilane reagent may be added to the reaction mixture at the end of step a) without performing an isolation step. The hydrogenation reaction may occur at a temperature between about 40° C. and about 60° C. To achieve this reaction temperature, the reaction mixture may be heated using a non-microwave heating source.

To conduct the reaction of step b), fresh hydrosilane reagent may be added to the reaction mixture in separate aliquots. The addition may occur 2, 3, 4 or 5 times. Aliquots of the fresh hydrosilane reagent may be added to the reaction mixture three times. When multiple separate aliquots are added to the reaction mixture, the aliquots may be added at 2 hour intervals. Following the final addition of hydrosilane reagent, the reaction mixture may be left overnight before proceeding to step c). The steps a) and b) may occur in the same vessel without isolating the products of step a) before performing the reaction of step b).

Once the hydrogenation reaction of step b) has completed, the cleavage step of step c) may be conducted. The cleavage reaction of step c) may use an acid capable of cleaving peptides from a solid support resin. Once cleaved, the product formed is a compound of Formula I. The compound of Formula I produced may be between 5 and 20 residues in length. The compound may be produced by solid-phase synthesis.

In one embodiment, the process of the present invention involves producing a compound of Formula I

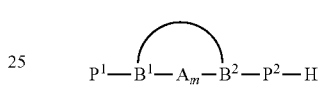

wherein: m is 3; each A is independently a naturally occurring amino acid residue; $B^1$ and $B^2$ are each substituted amino acid residues covalently coupled together by a saturated alkyl chain; $P^1$ and $P^2$ are each independently one or more amino acid residues, wherein $P^1$ has a terminal amino group and $P^2$ has a terminal carboxylic acid group; and H is hydrogen. The process comprises the steps of:

a) performing a metathesis reaction on a compound of general Formula II so as to form an intramolecular alkenyl chain between the $B^{1a}$ and $B^{2a}$ groups

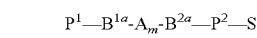

wherein: $B^{1a}$ is a group of Formula IIa

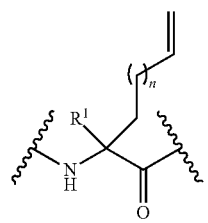

wherein $R^1$ is ethyl; $B^{2a}$ is a group of Formula IIb

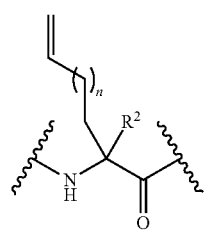

wherein $R^2$ is ethyl; the n of Formula IIa is 8 and the n of Formula IIb is 5; and S is a solid state resin; said reaction occurring between the alkenyl side chain of $B^{1a}$ and the alkenyl side chain of $B^{2a}$ so as to form an intramolecular alkenyl chain;

b) hydrogenating the carbon-carbon double bond formed in step a) so as to produce a saturated alkyl chain; and, c) cleaving the solid state resin material from $P^2$ so as to produce a compound of Formula I.

In the process of this embodiment, the process of step a) includes adding two aliquots of a ruthenium-based alkylidene catalyst to a suspension of the compound of Formula II, wherein the compound of Formula II is suspended in a halogenated alkane solvent, such as dichloroethane. The reaction mixture comprising the halogenated alkane solvent, the compound of Formula II and the ruthenium-based alkylidene catalyst is held at a temperature between 15° C. and 60° C. Following completion of the reaction of step a), between 2 and 3 aliquots of a neat trialkylhydrosilane reagent of general Formula [$R_3$SiH] is added, with 2 hours elapsing between each addition of the trialkylhydrosilane reagent. During step b), the temperature is held between 40° C. and 60° C., with the heating supplied by a source that is a non-microwave heating source. After the final addition of the trialkylhydrosilane reagent, an acid capable of cleaving the peptide from the solid state resin is added, resulting in the production of a compound of Formula I.

In another embodiment, the process of the present invention involves producing a compound of Formula I

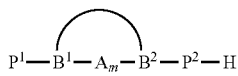

I wherein: m is 3; each A is independently a naturally occurring amino acid residue; $B^1$ and $B^2$ are each substituted amino acid residues covalently coupled together by a saturated alkyl chain; $P^1$ and $P^2$ are each independently one or more amino acid residues, wherein $P^1$ has a terminal amino group and $P^2$ has a terminal carboxylic acid group; and H is hydrogen. The process comprising the steps of:

a) performing a metathesis reaction on a compound of general Formula II so as to form an intramolecular alkenyl chain between the $B^{1a}$ and $B^{2a}$ groups

II wherein: $B^{1a}$ is a group of Formula IIa

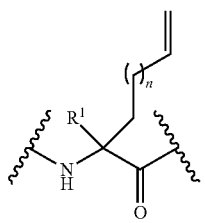

IIa wherein $R^1$ is alkyl; $B^{2a}$ is a group of Formula IIb

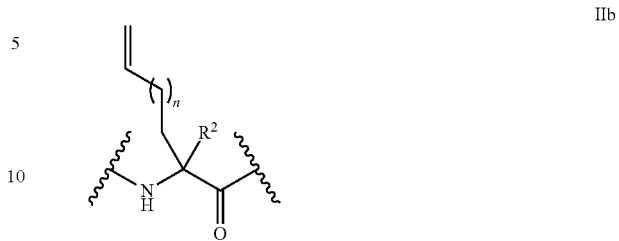

IIb wherein $R^2$ is alkyl; the n of Formula IIa is between 3 and 8 and the n of Formula IIb is between 2 and 5; and S is polystyrene; said reaction occurring between the alkenyl side chain of $B^{1a}$ and the alkenyl side chain of $B^{2a}$ so as to form an intramolecular alkenyl chain;

b) hydrogenating the carbon-carbon double bond formed in step a) so as to produce a saturated alkyl chain; and, c) cleaving the solid state resin material from $P^2$ so as to produce a compound of Formula I.

In the process of this embodiment, the process of step a) may include adding 4 aliquots of a Grubbs II catalyst to a suspension of the compound of Formula II, wherein the compound of Formula II may be suspended in dichloroethane. The reaction mixture comprising the halogenated alkane solvent, the compound of Formula II and the ruthenium-based alkylidene catalyst may be held at a temperature between 15° C. and 60° C. After the fourth aliquot of catalyst is added and the reaction of step a) may be complete or substantially complete, step b) begins with the addition of the first aliquot of triethylhydrosilane. A total of up to 3 aliquots of neat fresh triethylhydrosilane reagent may be added during this step, with each aliquot of triethylhydrosilane added at 2 hour intervals. During step b), the temperature may be held between 40° C. and 60° C., with the heating supplied by a source that is a non-microwave heating source. After the final addition of the trialkylhydrosilane reagent, trifluoroacetic acid may be added to cleave the peptide from the solid state resin, resulting in the production of a compound of Formula I. The resulting saturated stapled peptide may be between 10 and 15 residues in length.

In a second aspect of the present invention, there is provided a compound of Formula I that is obtained by the process according to the first aspect.

The following options may be used in conjunction with the second aspect, either alone or in any suitable combination.

The product that is obtained by the process of the first aspect may be a saturated stapled peptide. The saturated stapled peptide may be stabilised in an α-helical conformation, or at least a portion of the saturated stapled peptide may be stabilized in an α-helical conformation. A saturated stapled peptide in this context is one in which the linker which staples the peptide has no double or triple bonds. It will be understood that the stapled peptide may contain other unsaturation.

DEFINITIONS

The term "stapled peptides" as used herein refer to peptide or peptide-like chains respectively that incorporate two or more modified amino acids, such that when the peptide or peptide-like chain becomes a stapled peptide, the alkenyl chains of the substituted amino acids are covalently joined to produce an intramolecular alkenyl linker, which is then hydrogenated in the present invention, whereby the alkyl intramolecular linker constricts at least a portion of the peptide chain in at least one conformation.

The terminology "i, i+4" and "i, i+7" as used herein refer to the relative positions of the modified amino acid residues in the peptide chain in relation to each other, in which a first modified amino acid residue is at a position i, and the second modified amino acid residue is located a defined number of residues away in the chain. For example, an i, i+4 stapled peptide contains 3 amino acid residues between one modified amino acid residue (e.g., i) and the other modified amino acid residue (e.g., i+4) which is the fourth residue away from the i residue.

The term "oligopeptide", as used herein, refers to a peptide chain of between 2 and about 20 amino acid residues. The related term "polypeptide" as used herein refers to peptide chains that are greater than 20 amino acid residues in length, commonly up to about 50 residues in length.

The term "metathesis reaction", as used herein, refers to a reaction in which two alkene groups are converted to two new alkene groups by the exchange of carbon-carbon double bonds. This is commonly conducted in the presence of an alkylidene catalyst. This may be intramolecular.

Figure 1:
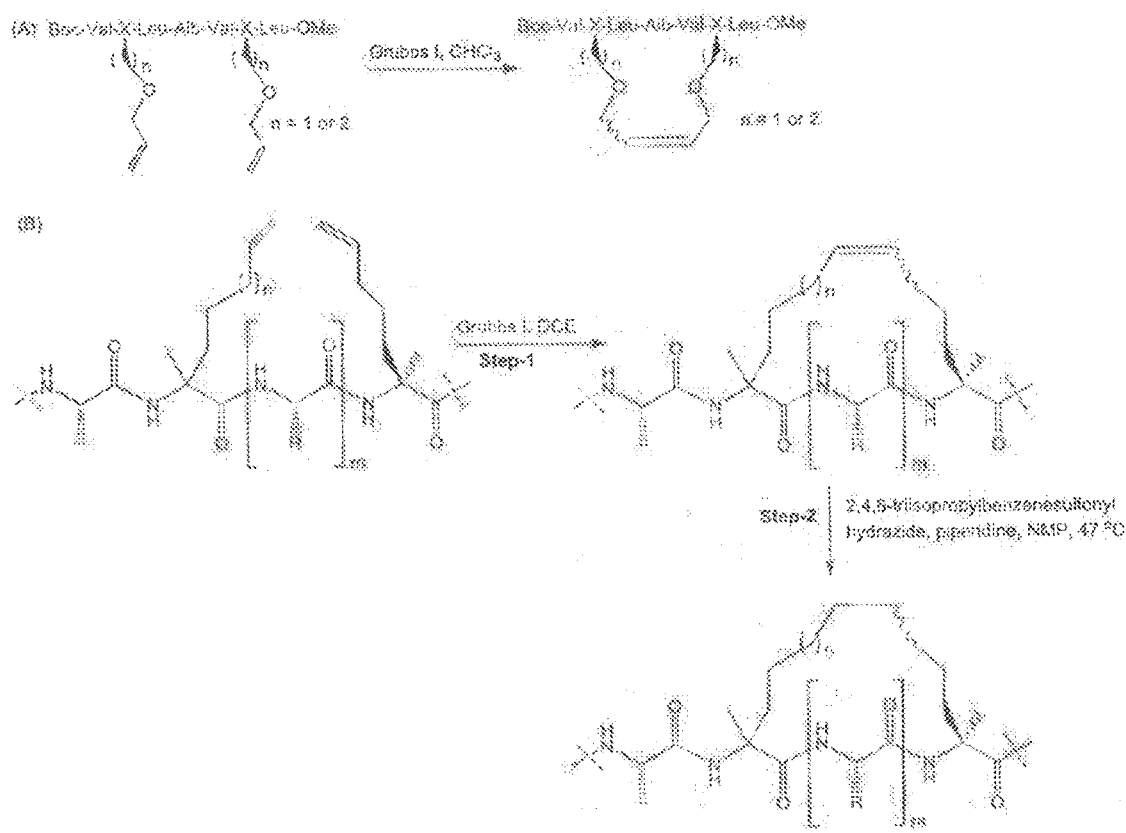
FIG. 1. Representative schemes of known methods for the preparation of stapled peptides.
Figure 2:
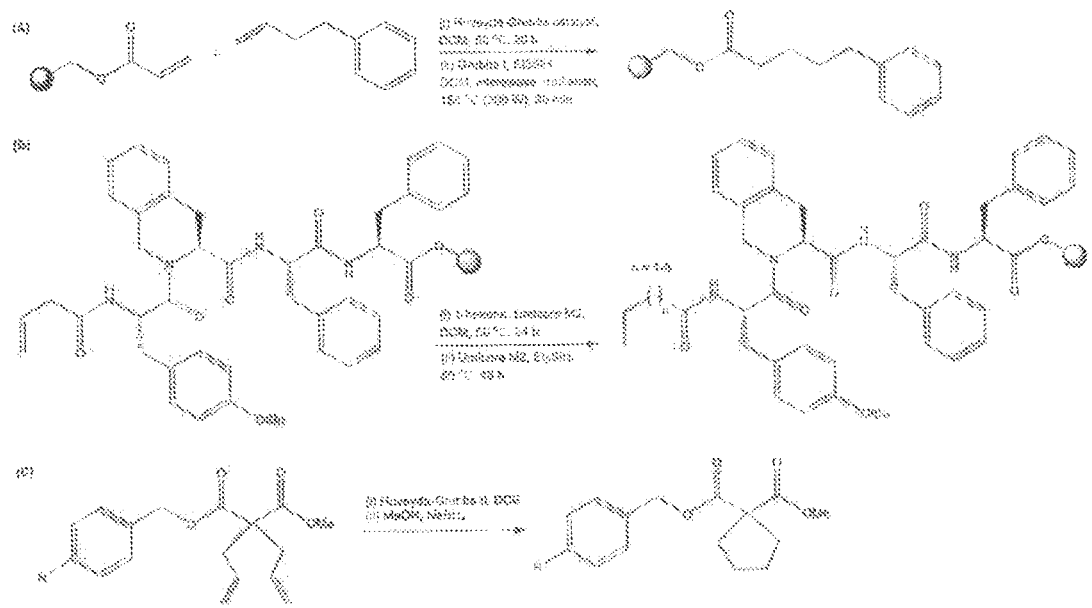
FIG. 2. Alternative tandem metathesis/reduction strategies using solid-state reagents and/or non-silane reagents.
Figure 3:
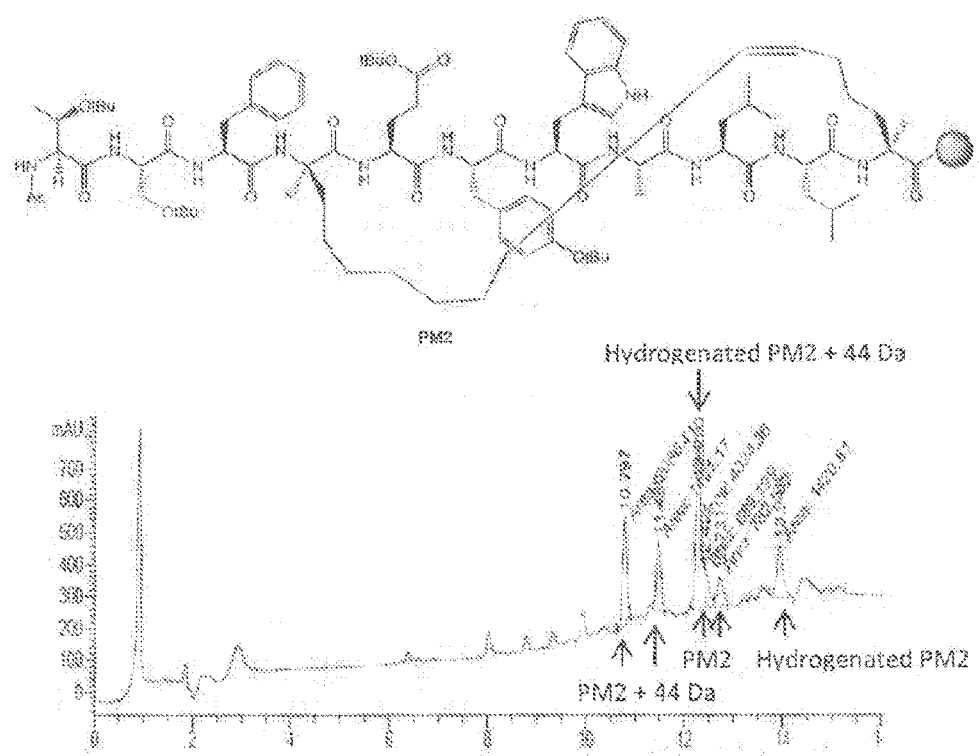
FIG. 3. Results of the attempted hydrogenation of stapled peptide PM2 after 4×2 h treatments with 2,4,6-triisopropylbenzenesulfonyl hydrazide as determined by HPLC.

The term "anchored", as used herein in reference to the alkylidene catalyst which forms the alkenyl linker, refers to a catalyst that comprises at least one bidentate or polydentate ligand coordinated to the catalytic metal centre, for example, the Hoveyda-Grubbs, Hoveyda-Grubbs II and Grubbs Z-selective catalysts of FIG. 1 are "anchored" catalysts. Likewise, the term "non-anchored" catalyst, as used herein, refers to a catalyst that does not comprise a bidentate or polydentate ligand, but rather contains all monodentate ligands coordinated to the catalytic metal centre. The terms "ligand", "bidentate" and "monodentate" all have the usual meanings that are well-known in coordination chemistry.

The term "one-pot synthesis" refers to a synthetic method that utilises several reaction steps, yet is conducted in a single reaction vessel, without any isolation steps occurring between reaction steps.

The term "amino acid" as used herein refers to organic compounds comprising a carboxyl group and an amino group. Such compounds are commonly able to polymerise via peptide bonds. The term "amino acid" is not intended to be limited to the common members of this class, the L-α-amino acids, and can include derivatives thereof.

The term "alkenyl", as used herein, refers to a hydrocarbon group derived from an alkene.

The term "between", as used herein, in reference to a range of values, includes the stated end points. Thus, "between" 1 and 6 includes 1, 2, 3, 4, 5 and 6.

The term "comprises" means "includes". Variations on the word "comprises", such as "comprising" and "comprise", have corresponding meanings. As used herein, the terms "including" and "comprising" are non-exclusive. As used herein, the terms "including" and "comprising" do not imply that the specified integer(s) represent a major part of the whole.

The term "consists essentially of" means "to the exclusion of other additional components purposefully added", or "only the following recited elements are intended to be present". Additional components may be present in the defined composition or device provided that they are not intentionally present.

DESCRIPTION OF EMBODIMENTS

The invention disclosed herein describes a solid-phase process for producing saturated stapled peptides. The process outlined herein avoids using costly, specialty reagents in order to produce saturated stapled peptides, which can be carried out as a 'one-pot' synthesis, further reducing production costs. Saturated stapled peptides may also show increased activity when compared to the identical, but unsaturated, stapled peptide.

The present specification describes a process for stapling a peptide that has been produced using solid-state synthesis methods, and then reducing the alkenyl linker whilst the peptide is still attached to the solid phase resin. Once removed from the solid phase, the saturated stapled peptide may be more biologically active than the unsaturated stapled peptide of the same sequence. As will be described in greater detail below and with reference to the Examples, the methods may be used to efficiently produce saturated stapled peptides without the need for expensive specialty reagents.

Peptide Chain

The saturated stapled peptides referred to herein are peptides which comprise an intramolecular alkyl linker between two different residues on the same peptide chain. The intramolecular linker acts to constrain the peptide chain, or at least a portion thereof, to a particular conformation, with the strength of the constraint depending on a number of factors, including the size of the peptide chain and the number of amino acid residues between the ends of the linker, relative to the length of the linker (i.e., the degree of conformation strain introduced by the restriction of the linker).

In the present invention, the saturated stapled peptide that includes an intramolecular alkyl linker is represented by Formula I:

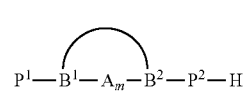

I

In the compound of Formula I, m is an integer between 1 and 8, optionally between 1 and 6, 2 and 7, 3 and 4, 2 and 5 or 5 and 8, e.g., 1, 2, 3, 4, 5, 6, 7, or 8. Each A is independently an amino acid residue, which may be either a naturally occurring amino acid, an unnaturally occurring amino acid, or a derivative thereof. Each A may be optionally substituted. $B^1$ and $B^2$ are each independently an amino acid residue, which may be a substituted naturally occurring amino acid or a substituted unnaturally occurring amino acid, which are covalently linked by an alkyl linker. $P^1$ and $P^2$ are each independently either an amino acid residue (e.g., a natural amino acid or an unnatural amino acid) or an oligopeptide chain or a polypeptide chain, wherein $P^1$ has a terminal amino group and $P^2$ has a terminal carboxyl group. H is hydrogen.

The peptide backbone of the stapled peptide has three regions comprising amino acids that are not involved in forming the intramolecular linker. These three regions are defined in both Formula I and Formula II as $P^1$, $P^2$ and A. $P^1$ may be an amino acid, or it may be an oligopeptide sequence, or it may be a polypeptide sequence. The $P^1$ residue or chain comprises one residue that is the N-terminus for the stapled peptide. The $P^1$ chain terminates in either a free amine group or a protected amine group. $P^2$ may also be an amino acid, or it may be an oligopeptide sequence, or it may be a peptide sequence. The $P^2$ residue or chain comprises one residue that is the C-terminus for the stapled peptide. The $P^2$ chain terminates in a carboxylic acid or an amide group. When $P^1$ and $P^2$ are peptide chains, there is no limit as to the length of either of these chains, provided that there is at least one residue present in each. A may be an amino acid, or it may be an oligopeptide sequence, or it may be a polypeptide sequence. A may comprise between 1 and 8 amino acid residues, as defined by m. Hence, m may be an integer between 1 and 8, for example between 1 and 6, 1 and 4, 4 and 8, 3 and 7 or 2 and 6, e.g., 1, 2, 3, 4, 5, 6, 7 or 8. The number of residues in A is limited by the maximum length of the linker able to be formed, and the linker must traverse the distance of A in order to form the stapled peptide.

The amino acids of the $P^1$, $P^2$ and A groups, whether a single residue, an oligopeptide or a polypeptide, may each be selected from a naturally occurring L-α-amino acid (e.g., L-α-arginine, L-α-histidine, L-α-lysine, L-α-aspartic acid, L-α-glutamic acid, L-α-serine, L-α-threonine, L-α-asparagine, L-α-glutamine, L-α-cysteine, L-α-selenocysteine, L-α-glycine, L-α-proline, L-α-alanine, L-α-valine, L-α-isoleucine, L-α-leucine, L-α-methionine, L-α-phenylalanine, L-α-tyrosine or L-α-tryptophan) or an unnatural amino acid (e.g., D-α-amino acid, an L-β-amino acid, a D-β-amino acid, an L-γ-amino acid, a D-γ-amino acid, an L-δ-amino acid, a D-δ-amino acid) or derivatives thereof. Each amino acid, whether natural or unnatural, may be optionally substituted. Each of $P^1$, $P^2$ and A may contain a combination of natural L-α-amino acid and unnatural amino acids, or they may each contain a single class of amino acid.

The linker between $B^1$ and $B^2$ of Formula I is formed from the two alkenyl chains present on the side chains of the substituted amino acid residues, as shown in Formula II. Whilst the lengths of the alkyl portions of each of the alkenyl chains are defined as n in both Formula IIa and Formula ID, both of the n values in these formulae are independently selected from an integer between 0 and 12 (e.g., between 0 and 8, 0 and 6, 6 and 12, 4 and 10, 3 and 11, 2 and 8 or 4 and 8, or they may each independently be 0, 1, 2, 3, 4, 5, 6, 7, 8, 9, 10, 11 or 12) and need not necessarily be the same, and commonly are different. The skilled addressee would appreciate that each n value can be selected depending on the particular peptide chain sequence and the particular geometry of the folded peptide.

In order to produce a stapled peptide chain of Formula I, a peptide chain is first formed that comprises at least two substituted amino acid residues capable of being covalently linked. In particular, the substituted amino acid residues each include an alkenyl chain attached to the α-carbon of the amino acid. The substituted amino acids can be incorporated into a peptide chain by using standard peptide synthesis methods such as solid-phase peptide synthesis which are well-known in the art.

Once the peptide chain is formed, it will contain at least two substituted amino acid residues that are a defined distance apart. For instance, the modified amino acid residues may be separated by 6 amino acid residues to form an i, i+7 stapled peptide, or they may be separated by 4 amino acid residues to form an i, i+5 stapled peptide. Other appropriate arrangements of residues will be known by the skilled addressee, or may become known.

Peptide Stapling Method

As discussed above, in order to form a compound of Formula I, a peptide chain is formed that comprises at least two substituted amino acid residues capable of being covalently linked. The two substituted amino acids both include an alkenyl chain attached to the α-carbon, whereby the alkenyl carbon-carbon double bond is located at the terminus of the chain. In the present invention, this intramolecular linker is formed by reacting the alkenyl-terminating chains of the substituted amino acids.

In the present invention, to produce a compound of Formula I, the starting material is a compound of Formula II:

$$P^1-B^{1a}-A_m-B^{2a}-P^2-S \qquad \qquad II$$

wherein $B^{1a}$ is a group of Formula IIa:

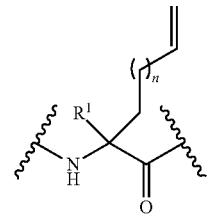

and $B^{2a}$ is a group of Formula IIb:

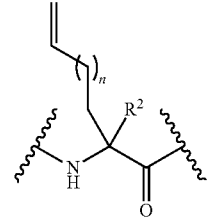

Each n is independently an integer between 0 and 12, or between 0 and 6, 6 and 12, 4 and 8, 2 and 10 or 4 and 12, e.g., 0, 1, 2, 3, 4, 5, 6, 7, 8, 9, 10, 11 or 12. Each $R^1$ and $R^2$ is an optionally substituted alkyl group, such as methyl, ethyl, propyl, butyl or pentyl. $R^1$ and $R^2$ may be the same or they may be different. $R^1$ and $R^2$ may each be methyl. S is a solid state resin from which the saturated stapled peptide will be released. The solid state resin may be a polymeric material or it may be any other suitable material. It may for example be polystyrene, polyamide, polyethylene glycol, a polyethylene glycol resin, or it may be a blend of any two or more than two of the above polymers. As can be clearly seen, both Formula IIa and IIb comprise alkenyl chains that terminate in a carbon-carbon double bond.

In order to produce the intramolecular linker, in a first reaction step, herein step a), the terminal alkenyl groups of the $B^{1a}$ and $B^{2a}$ groups (i.e., Formula IIa and IIb) are coupled together to form the unsaturated intramolecular alkenyl linker, hence constraining the peptide. As would be clear to the skilled person, the $R^1$ and $R^2$ groups of the $B^{1a}$ and $B^{2a}$ moieties respectively are maintained in the stapled peptide (i.e. after formation of the intramolecular linker) at the $B^1$ and $B^2$ positions, and contribute to the stereochemistry of the intramolecular linker. One approach for carrying out this step is to perform a metathesis reaction. Such reactions are well known in the art of hydrocarbon chemistry. The resultant intramolecular alkenyl linker contains a single carbon-carbon double bond at the site where the two chains were joined together, with the remainder of the linker chain being saturated alkyl carbons. Whilst in this unsaturated state, the carbon-carbon double bond may be in either the (E)-configuration or the (Z)-configuration. This may be of little consequence to the present invention, which discloses a saturated stapled peptide, whereby this double bond is hydrogenated and the linker is an alkyl chain.

The reaction of step a) may be conducted in the presence of a catalyst. The catalyst is selected to assist the reaction between the terminal alkenyl groups to form the intramolecular linker. The catalyst may be a catalyst known to catalyze a metathesis reaction. It may comprise a catalytic metal atom. It may be an anchored catalyst (e.g., a catalyst with at least one bidentate ligand coordinating to the metal atom). It may be a non-anchored catalyst (e.g., a catalyst with all monodentate ligands coordinating to the metal atom). The catalyst may be an alkylidene catalyst. It may be a non-anchored alkylidene catalyst. An alkylidene catalyst is a catalyst that catalyses reactions between alkenes. The catalyst may comprise ruthenium or it may comprise molybdenum as the catalytic metal atom. The catalyst may for example be a non-anchored ruthenium catalyst (e.g., a Grubbs I catalyst or a Grubbs II catalyst), or it may be an anchored ruthenium catalyst (e.g., a Hoveyda-Grubbs I catalyst, a Hoveyda-Grubbs II catalyst or a Grubbs Z catalyst).

The metathesis reaction of step a) may be carried out by adding an aliquot of the dissolved catalyst to a suspension of a peptide chain bound to a solid support, as described above as Formula II. The method of step a) may include a single addition of an aliquot of catalyst. Where the catalyst may degrade at the reaction conditions or otherwise reduce in efficacy during the reaction, fresh aliquots of catalyst may be added to the reaction mixture to ensure as high a yield of the peptide of Formula I as possible. Where multiple aliquots are added, it may involve the addition of 2, 3, 4, 5 or more than 5 aliquots of catalyst, before the stapled peptide is cleaved from the solid state resin and collected. The catalyst added may be fresh, regenerated or used. Two aliquots of fresh catalyst may be added to the reaction mixture. The time between aliquot additions may be relatively short (e.g., between about 1 and 60 minutes, such as 1, 2, 3, 4, 5, 10, 15, 20, 35, 30, 35, 40, 45, 50, 55 or 60 minutes) or it may be longer (e.g., between 1 and 4 hours, such as about 1, 1.5, 2, 2.5, 3, 3.5 or 4 hours). The time between multiple aliquots may be the same throughout the method of step (a) or it may vary from aliquot to aliquot. The volume of the aliquots may be the same or they may be different. The solvent that the catalyst is dissolved in may be the same as the solvent that the compound of Formula II is immersed in, or they may be different. The solvent used may be a halogenated alkane, for example it may be dichloroethane. If the solvents are different, they may be miscible.

The reaction of step a) may be conducted at a temperature of between 15° C. and about 60° C. (e.g. between about 15° C. and about 30° C., or between about 30° C. and 60° C., 20° C. and 40° C., 20° C. and 50° C., 30° C. and 40° C., or 25° C. and 45° C., e.g., at about 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59 or 60° C.). The reaction may be conducted at room temperature.

Hydrogenation Reaction

Once the peptide has been stapled as a result of step a), the second reaction step, herein step b), is the hydrogenation of the carbon-carbon double bond located on the unsaturated alkenyl linker, to produce a saturated stapled peptide that is still bound to the solid state resin.

Methods of hydrogenating a carbon-carbon double bond are known in the art. One example is to use a hydrosilane reagent to hydrogenate a carbon-carbon double bond. The hydrosilane reagent may be of general formula $SiH_nR_{4-n}$, wherein n is an integer between 1 and 4 (e.g., 1, 2, 3 or 4). Each R may independently be any organic group that does not preclude the carbon-carbon double bond from interacting with the position of the at least one hydrogen on the central silicon atom, which is believed to be the active site of the hydrosilane reagent. R may be alkyl (e.g., methyl, ethyl, propyl, butyl or pentyl) or it may be aryl (e.g., phenyl, naphthyl, furanyl, pyridinyl or thiophenyl). R may be ethyl. The hydrosilane may be a trialkylhydrosilane of general formula $[R_3SiH]$. The trialkylhydrosilane reagent may be triethylhydrosilane, wherein each R is ethyl.

The reaction of step b) can be conducted sequentially with, or concomitantly with, the reaction of step a). The reactions of step a) and step b) may overlap (i.e., step b) may begin before the completion of step a)) or they may be isolated (i.e., step a) is brought to substantial completion before step b) begins). For instance, the hydrosilane reagent of step b) may be added to the reaction mixture after the addition of the last aliquot of catalyst is added in the first step, and/or following the completion of the reaction of step a), resulting in a sequential reaction scheme. It may be added after any earlier aliquot of catalyst in step a), allowing for both reactions to occur concomitantly. The hydrosilane reagent may be added together with the first aliquot of catalyst. The reactions of step a) and step b) can occur in the same vessel, without requiring the isolation of the product of step a) for use as a reagent in step b) in a 'one-pot' synthesis. Hence, the solvents used to suspend the compound of Formula II, and dissolve the catalyst, should be miscible with each other and able to dissolve the hydrosilane reagent when used neat. They may be in the same solvent. Alternatively, the product of step a) can be isolated and purified before use in step b), in which case the solvent systems used to suspend the solid state resin-bound peptides in each step may be different.

The addition of the hydrosilane reagent of step b) may be performed by the addition of a single aliquot at the beginning of the reaction step, or it may be added in separate, multiple aliquots. When multiple aliquots are used to replenish the hydrosilane reagent during the progression of the reaction of step b), the aliquots may be added at regular intervals, or they may be added irregularly. When aliquots are added at regular intervals, the time between aliquot additions may be relatively short (e.g., between about 1 and 60 minutes, such as 1, 2, 3, 4, 5, 10, 15, 20, 35, 30, 35, 40, 45, 50, 55 or 60 minutes) or it may be longer (e.g., between 1 and 4 hours, such as about 1, 1.5, 2, 2.5, 3, 3.5 or 4 hours). The time between multiple aliquots may be the same throughout the method of step (a) or it may vary from aliquot to aliquot. The time interval between aliquot additions may be 2 hours. Aliquots of hydrosilane reagent may be added 2, 3, 4, 5 or more than 5 times during the course of the reaction of step b), for instance 3 aliquots may be added to the reaction mixture during the progression of the reaction of step b).

After the addition of the last aliquot of step b), the reaction mixture may be left for a period of time to allow for the completion, or substantial completion, of the reaction. The reaction mixture may be held at the reaction temperature, or it may be allowed to cool to a room temperature. During this period after the addition of the final aliquot of hydrosilane reagent, the reaction mixture may be continuously stirred after the final addition of hydrosilane reagent, or it may be exposed to a combination of stirring and non-stirring during this time. The period of time between the addition of the final hydrosilane aliquot and the commencement of the end of the process of step b) may be relatively short (e.g., between about 10 minutes and about 2 hours, such as 10, 15, 20, 35, 30, 35, 40, 45, 50, 55, 60, 70, 80, 90, 100, 110 or 120 minutes) or it may be longer (e.g., between 2 and 24 hours, such as about 2, 3, 4, 5, 6, 7, 8, 9, 10, 11, 12, 13, 14, 15, 16, 17, 18, 19, 20, 21, 22, 23 or 24 hours). The time period may be overnight.

The hydrogenation reaction of step b) may be conducted at a temperature of between about 40° C. and about 60° C. or between about 40° C. and 60° C., about 50° C. and 60° C., about 40° C. and 50° C., about 45° C. and 55° C., about 40° C. and 55° C. about 45° C. and 60° C., e.g., at about 40, 41, 42, 43, 44, 45, 46, 47, 48, 49, 50, 51, 52, 53, 54, 55, 56, 57, 58, 59 or 60° C. To conduct the reaction of step b) at this temperature, any suitable heating source may be used. The heating source may be any source that is not a microwave heating source. The heating source may be radiative, or it may be convective.

Product

In a third step, herein step c), the saturated stapled peptide formed in the process of step b), being a compound of Formula I, is cleaved from the solid state resin. This cleavage can be conducted by using any reagent capable of cleaving the $P^2$—S bond. The cleavage reagent may be an acid. It may be a reagent commonly known for use in such cleavage reactions, such as hydrogen fluoride or trifluoroacetic acid, which break the $P^2$—S bond to produce a free compound of Formula I with a protonated C-terminal. The solid state resin may be a polymeric material. It may for example be polystyrene, polyamide, polyethylene glycol, a polyethylene glycol resin, or it may be a blend of two or more than two of the above polymers.

The saturated stapled peptide of Formula I produced by this process may have more than 5 amino acid residues in the peptide chain, including the substituted residues that form the intramolecular linker. The saturated stapled peptide may be of between about 5 and about 100 residues in length, for instance it may be between 5 and 80, 10 and 80, 20 and 80, 30 and 70, 40 and 60, 15 and 75, 25 and 50 or between 5 and 10, e.g., about 5, 6, 7, 8, 9, 10, 12, 20, 25, 30, 35, 40, 45, 50, 55, 60, 65, 70, 75, 80, 85, 90, 95, or 100 residues in length. The saturated stapled peptide may be longer than 100 residues. The saturated peptide may have more than one alkyl linker in the peptide chain.

The compound of Formula I produced by the method described herein may be a stapled peptide. The skilled addressee would understand that as the compound of Formula I contains at least two modified amino acid residues and an intramolecular alkenyl linker, it is more strictly a peptide analogue, rather than a peptide per se. However, the term "stapled peptide" is used herein to describe such peptide chains comprising an intramolecular linker. The stapled peptide, may contain a secondary structure which is preserved due to the presence of the bridging alkyl linker. This secondary structure that is preserved is found between the modified amino acids which become linked (i.e., $A_m$ in Formula I). For example, the secondary structure may be an α-helical region that is bridged by the intramolecular alkenyl linker, thereby stabilising the α-helical region and preventing the denaturing of this secondary structure of the stapled peptide. Other secondary structures, such as β-sheets or peptide loops, may be preserved by forming an alkyl linker.

The present invention may be better understood by the skilled addressee with reference to the following illustrative, and non-limiting, examples.

EXAMPLES

Example 1

A method of one-pot ring closing metathesis-hydrogenation is described below which details a solid-phase method of preparing saturated stapled peptides by using a one-pot ring closing metathesis-hydrogenation sequence. Whilst transfer hydrogenation may be achieved using sodium borohydride and variants, it is believed to be most effective with hydrosilanes, such as triethylhydrosilane, as the reagent. This simple and practical protocol, as exemplified below, provides a useful complement to the current state of art in stapled peptide synthesis and modification.

In this method, following completion of ruthenium-catalysed metathesis, the resin-bound unsaturated stapled peptide was treated with neat triethylhydrosilane at 50° C. to achieve solid-phase transfer hydrogenation. After periodic replenishments of reagents (every 2 hours for the first 4 hours) and overnight reaction, the corresponding reduced peptide was recovered in good yield. Initial experiments indicated the use of triethylhydrosilane is compatible with multiple ruthenium-based catalysts. The utility of the method has been demonstrated on 14- and 16-mer peptides to yield the corresponding cyclic α-helix stabilised stapled peptides.

As sodium borohydride and $Et_3SiH$ were found to be effective hydrogen transfer reagents, experiments were focused on the compatibility of these reagents for use with stapled peptide systems. The results of these experiments are found below, and in Table 1.

Accordingly, linear ATSP-7041 (Ac-LT(tBu)F(R8)E(tBu)Y(tBu)W AQ(Trt)(cba)(S5)S(tBu)AA-NH2) and VIP116 (Ac-K(Boc)(Ahx)T(tBu)S(tBu)F(R8)E(tBu)Y(tBu)WALL(S5)E(Trt)N(Trt)F-NH2) peptide constructs were subjected to 2 metathesis cycles with Grubbs II catalyst in DCE to form the unsaturated intramolecular linker. Thereafter, $NaBH_4$ (2 equivalents) and MeOH were directly added to the ruthenium mixture (entry 2, Table 1). Mini cleavages conducted at T=2 h, 4 h and overnight after the addition of $NaBH_4$ showed little hydrogenated product had formed along with significant amounts of a side product (the molecular weight corresponded to addition of methanol across the double bond). Addition of fresh reagents at T=2 h and 4 h had little effect (entry 3, Table 1). Similar observations were found with the more soluble $Bu_4NBH_4$ (entries 4-5, Table 1). Increasing the reaction temperature to 50° C. (entry 6, Table 1) gave rise to the desired hydrogenated products in comparable yields to standard diimide conditions (entry 1, Table 1).

Conversely, silane-mediated hydrogenations at room temperature were also low yielding (entries 7-9, Table 1). For ATSP-7041, use of phenylsilane (entry 9, Table 1) led to the exclusive formation of a side product. In comparison to diimide conditions, when ATSP-7041 and VIP116 were treated with 5 equivalents of $Et_3SiH$ at 50° C. with occasional replenishment of reagents, product conversion increased by 60%.

Additional experiments were conducted investigating the scope of suitable metathesis catalysts. To our surprise, Grubbs I, Hoveyda-Grubbs I and Hoveyda-Grubbs II catalysts also mediated sequential ring-closing metathesis-reductions.

TABLE 1

| entry | Hydrogenation conditions | ATSP-7041 (% conversion)[b,c] | | | VIP116 (% conversion)[b,c] | | |
|---|---|---|---|---|---|---|---|
| | | 2 h | 4 h | Overnight | 2 h | 4 h | Overnight |
| 1 | 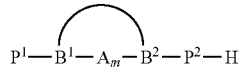 Piperidine, NMP, 60° C[a] | 16 | 27 | 39 | 28 | 37 | 45 |
| 2 | NaBH$_4$, MeOH, rt | 10 (9) | 14 (13) | 22 (21) | 15 | 15 | 15 |
| 3 | NaBH$_4$, MeOH, rt$^2$ | 8 (33) | 17 (33) | 22 (28) | 15 (12) | 22 (14) | 30 (14) |
| 4 | Bu$_4$NBH$_4$, MeOH, rt | 9 (39) | 9 (39) | 9 (39) | 19 (28) | 20 (29) | 22 (29) |
| 5 | Bu$_4$NBH$_4$, MeOH, rt$^2$ | 7 (21) | 14 (21) | 23 (18) | 21 | 31 | 31 |
| 6 | Bu$_4$NBH$_4$, MeOH, 50° C.[a] | 25 | 41 | 41 | 15 (6) | 29 (15) | 35 (19) |
| 7 | PMHS, rt | 5 | 6 | 8 | 3 | 5 | 13 |
| 8 | PhSiH$_3$, rt | 0 (32) | 0 (32) | 0 (32) | 0 | 0 | 0 |
| 9 | Et$_3$SiH, rt | 9 | 15 | 21 | 0 | 11 | 13 |
| 10 | Et$_3$SiH, 50° C.[a] | 12 | 38 | 71 | 14 | 29 | 73 (14) |
| 11 | Grubbs I then Et$_3$SiH, 50° C.[a] | 52 | 64 | 83 | 34 | 57 | 81 |
| 12 | Hoveyda-Grubbs I then Et$_3$SiH, 50° C.[a] | 33 | 42 | 75 | 54 (13) | 64 (12) | 73 (14) |
| 13 | Hoveyda-Grubbs II then Et$_3$SiH, 50° C.[a] | 44 | 72 | 84 | 50 | 50 | 84 |

Solid-supported one-pot ring-closing metathesis-hydrogenation. [a]fresh reagents were replenished at T = 2 h and 4 h. [b]Percent conversion = product/(product + starting material) as determined by reverse phase HPLC. [c]Data in brackets represents the yields of side products.

Example 2

In order to evaluate the influence of the geometry of the hydrocarbon bridge on the biological activities of stapled peptides, saturated stapled peptides were prepared using the described protocol and their p53 activity were compared to the corresponding unsaturated stapled peptides.

Figure 4:
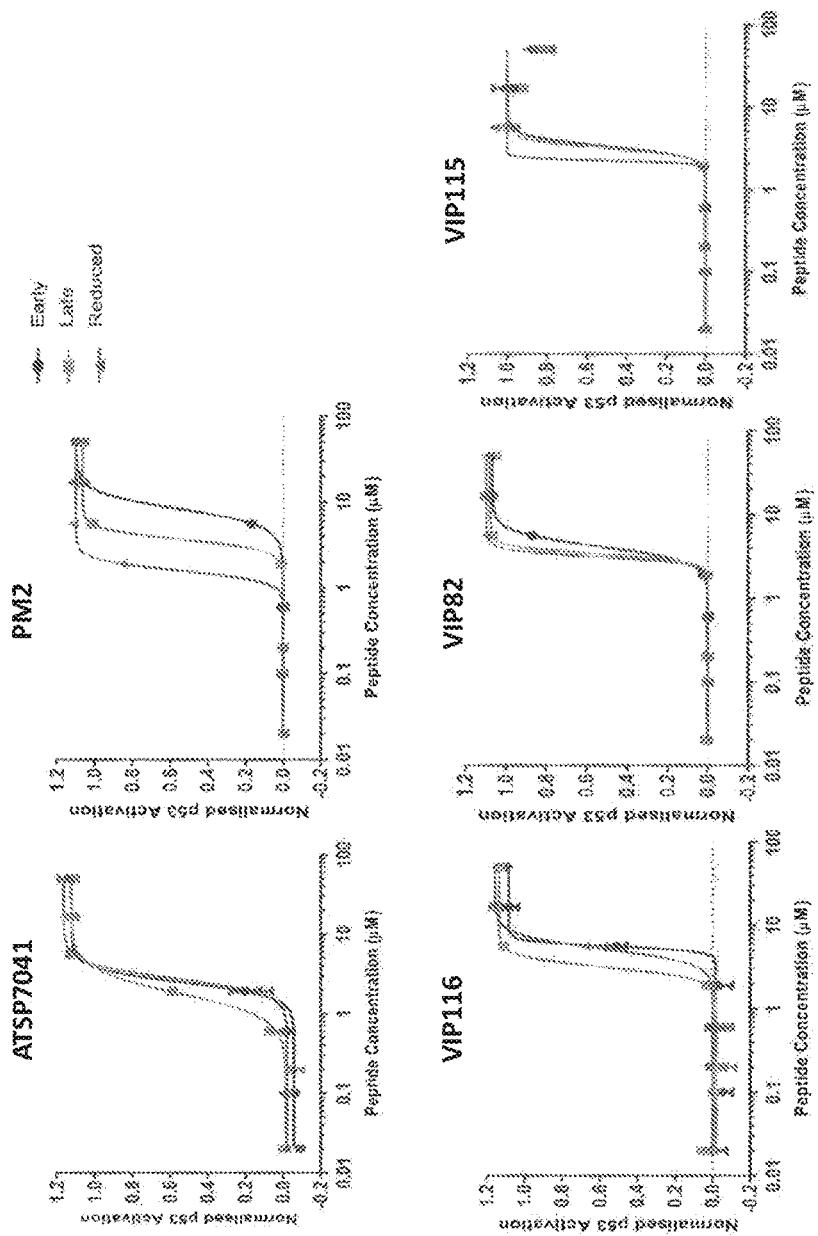
FIG. 4. Results of an in vitro study to determine the effect of saturating the intramolecular linker on the biological response to a range of stapled peptides, wherein the study comprised the titration of stapled peptide geometric isomers and reduced (i.e. saturated) stapled peptides onto T22 p53 reporter cell lines in the presence of 2% FCS.

15 stapled peptide variants were titrated onto T22 p53 reporter cell lines in 2% serum conditions (FIG. 4). These variants are the two geometric isomers (i.e., where the intramolecular linker contains a carbon-carbon double bond which may be either the (E) or (Z) isomer), and the reduced, saturated stapled isomer, for five different stapled peptides. The five stapled peptides in this study are:

ATSP-7041=Ac-LTF(R8)EYWAQ(cba)(S5)SAA-NH$_2$
PM2=Ac-TSF(R8)EYWALL(S5)-NH$_2$
VIP116=Ac-K(Ahx)TSF(R8)EYWALL(S5)ENF-NH$_2$
VIP182=Ac-KK(Ahx)TSF(R8)EYWALL(S5)ENF-NH$_2$
VIP116=Ac-KKK(Ahx)TSF(R8)EYWALL(S5)ENF-NH$_2$ From the study, it can be seen that the reduction of the staple olefin (represented by the triangle points) did not lead to attenuated p53 activation. In some cases, reduction had improved the potency of the peptide compared to the early and late eluting isomer, whereby the (Z)-isomer is the early eluting isomer.

The invention claimed is:

1. A process for producing a compound of general Formula I:

$$P^1\text{—}B^1\text{—}A_m\text{—}B^2\text{—}P^2\text{—}H \qquad \text{I}$$

wherein:
   m is an integer between 1 and 8;
   each A is independently an amino acid residue;
   B$^1$ and B$^2$ are each substituted amino acid residues covalently coupled together by a saturated alkyl chain;
   P$^1$ and P$^2$ are each independently one or more amino acid residues, wherein P$^1$ has a terminal amino group and P$^2$ has a terminal carboxylic acid group; and,
   H is hydrogen;

said process comprising the steps of:
  a) performing a metathesis reaction on a compound of general Formula II so as to form an intramolecular alkenyl chain between the B$^{1a}$ and B$^{2a}$ groups $$P^1\text{—}B^{1a}\text{—}A_m\text{—}B^{2a}\text{—}P^2\text{—}S \qquad \text{II}$$

wherein:
   B$^{1a}$ is a group of Formula IIa

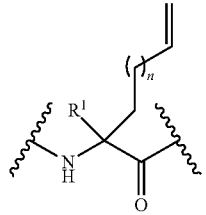

IIa wherein R$^1$ is alkyl;
B$^{2a}$ is a group of Formula IIb

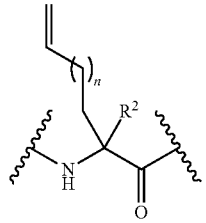

IIb wherein R$^2$ is alkyl;

each n is independently an integer between 0 and 12; and

S is a solid state resin;

said reaction occurring between the alkenyl side chain of $B^{1a}$ and the alkenyl side chain of $B^{2a}$ so as to form an intramolecular alkenyl chain;

b) hydrogenating the carbon-carbon double bond formed in step a) so as to produce a saturated alkyl chain, wherein the hydrogenating is conducted with a hydrosilane reagent, wherein the hydrosilane reagent is triethylsilane; and, c) cleaving the solid state resin material from $P^2$ so as to produce a compound of Formula I.

2. The process of claim 1 wherein m is an integer between 1 and 6.

3. The process of claim 1 wherein each A is independently a naturally occurring L-α-amino acid.

4. The process of claim 1 wherein at least one A is an unnatural amino acid.

5. The process of claim 1 wherein $R^1$ is methyl.

6. The process of claim 1 wherein $R^2$ is methyl.

7. The process of claim 1 wherein S comprises a polymeric material.

8. The process of claim 1 wherein step a) is conducted in the presence of a catalyst.

9. The process of claim 8 wherein the catalyst comprises ruthenium.

10. The process of claim 8 wherein fresh catalyst is added to the compound of Formula II in separate aliquots, said addition occurring 2, 3, 4 or 5 times.

11. The process of claim 10 wherein fresh catalyst is added to a compound of Formula II twice before conducting step b).

12. The process of claim 8 wherein the metathesis reaction occurs at a temperature between 15° C. and 60° C.

13. The process of claim 1 wherein the hydrosilane reagent is added to the reaction mixture concomitantly with the catalyst.

14. The process of claim 1 wherein the hydrogenation reaction of step b) is conducted at a temperature between about 40° C. and about 60° C.

15. The process of claim 14 comprising heating the reaction mixture to said temperature using a non-microwave heating source.

16. The process of claim 1 wherein fresh hydrosilane reagent is added to the reaction mixture in separate aliquots, said addition occurring 2, 3, 4 or 5 times.

17. The process of claim 16 wherein aliquots of fresh hydrosilane reagent are added to the reaction mixture three times.

18. The process of claim 17 wherein the aliquots are added at 2 hour intervals.

19. The process of claim 17 wherein the reaction mixture is left overnight after the third aliquot addition before conducting step c).

20. The process of claim 1 wherein steps a) and b) occur in the same vessel without isolating the products of step a) before performing the reaction of step b).

21. The process of claim 1 wherein step c) uses an acid capable of cleaving peptides from a solid support resin.

22. The process of claim 1 wherein the compound of Formula I produced is between 5 and 20 residues in length.

23. The process of claim 1 wherein a compound of Formula II is produced by solid-phase peptide synthesis.

* * * * *